(12) United States Patent
Moenkemoeller

(10) Patent No.: US 9,880,139 B2
(45) Date of Patent: Jan. 30, 2018

(54) $CO_2$-CONCENTRATION SENSOR FOR INTERIOR USE

(71) Applicant: paragon ag, Delbrueck (DE)

(72) Inventor: Ralf Moenkemoeller, Bielefeld (DE)

(73) Assignee: paragon AG, Delbrueck (DE)

( * ) Notice: Subject to any disclaimer, the term of this patent is extended or adjusted under 35 U.S.C. 154(b) by 276 days.

(21) Appl. No.: 14/859,808

(22) Filed: Sep. 21, 2015

(65) Prior Publication Data

US 2016/0091472 A1 Mar. 31, 2016

(30) Foreign Application Priority Data

Sep. 30, 2014 (DE) .......................... 10 2014 014 557

(51) Int. Cl.
*G01M 17/00* (2006.01)
*G01N 33/00* (2006.01)
*G01L 11/02* (2006.01)

(52) U.S. Cl.
CPC .......... *G01N 33/0006* (2013.01); *G01L 11/02* (2013.01); *G01N 33/004* (2013.01)

(58) Field of Classification Search
USPC ...................................................... 73/117.01
See application file for complete search history.

(56) References Cited

U.S. PATENT DOCUMENTS

| 4,742,761 | A | * | 5/1988 | Horstman | B64D 13/04 |
| | | | | | 128/205.26 |
| 5,925,831 | A | * | 7/1999 | Storsved | A61B 5/087 |
| | | | | | 128/204.23 |
| 6,659,962 | B2 | * | 12/2003 | Ricciardelli | A61B 5/087 |
| | | | | | 600/533 |
| 8,143,580 | B1 | * | 3/2012 | Wong | G01N 21/3504 |
| | | | | | 250/338.5 |
| 9,709,498 | B2 | * | 7/2017 | Moenkemoeller | G01N 21/61 |
| 2007/0279633 | A1 | * | 12/2007 | Yi | G01N 21/031 |
| | | | | | 356/432 |
| 2011/0049342 | A1 | * | 3/2011 | Tsao | G01N 21/274 |
| | | | | | 250/252.1 |
| 2012/0078532 | A1 | * | 3/2012 | Forsyth | G01N 21/274 |
| | | | | | 702/24 |
| 2013/0008224 | A1 | * | 1/2013 | Stormbom | G01N 21/274 |
| | | | | | 73/1.06 |
| 2016/0018321 | A1 | * | 1/2016 | Moenkemoeller | G01N 21/3504 |
| | | | | | 250/341.1 |
| 2016/0018330 | A1 | * | 1/2016 | Moenkemoeller | G01N 21/3504 |
| | | | | | 250/341.1 |

* cited by examiner

*Primary Examiner* — Eric S McCall
(74) *Attorney, Agent, or Firm* — Andrew Wilford

(57) ABSTRACT

A sensor arrangement for determining the $CO_2$ concentration in an interior space has an NDIR sensor unit that can determine the number of $CO_2$ molecules on an optical measuring section and therefrom the $CO_2$ concentration in an interior space. The sensor arrangement further has an evaluation unit that can calculate the air pressure from measurement values of the NDIR sensor unit and that can carry out an air-pressure compensation on the basis of the value calculated for the air pressure or of an air pressure correction value calculated therefrom for the measurement value of the $CO_2$ concentration determined by the NDIR sensor unit.

11 Claims, 1 Drawing Sheet

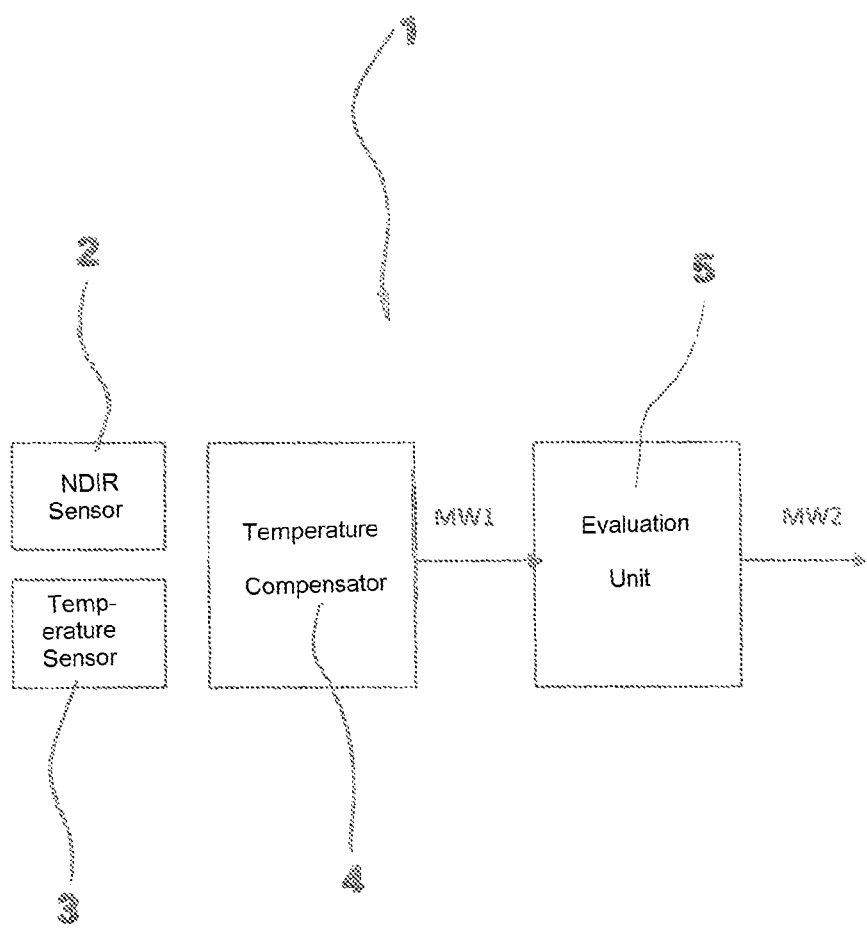

$CO_2$-CONCENTRATION SENSOR FOR INTERIOR USE

FIELD OF THE INVENTION

The present invention relates to a sensor for $CO_2$ concentration. More particularly this invention concerns such a sensor for interior use.

BACKGROUND OF THE INVENTION

The invention relates to a sensor arrangement for determining the $CO_2$ concentration in an interior space, with an NDIR sensor unit that can determine the number of $CO_2$ molecules on an optical measuring section and therefrom the $CO_2$ concentration in the interior space.

Such sensor arrangements for determining the $CO_2$ concentration in an interior space are frequently used for example in vehicles that travel at different elevations in relation to sea level. For example, there are operating profiles for motor vehicles that are to be operable at elevations between −400 m above sea level to +6000 m above sea level. At an elevation of approximately +5500 m above sea level, the air pressure is already reduced by approximately 50% compared with the standard value for temperature and pressure (STP). Accordingly then non-acceptable measurement deviations occur in the determining of the $CO_2$ concentration.

Measures known from the prior art for determining the pressure for carrying out a pressure compensation involve considerable costs, because pressure sensors, for example compared to temperature sensors, are considerably more cost-intensive. Therefore, in stationary sensor arrangements a pressure compensation is dispensed with, that in view of the comparatively small changes in air pressure that, in relation to STP (1013.25 mbar, 0 degrees C.) amount to ±30 Pa and accordingly in NDIR sensor units can lead to measurement deviations of approximately ±3%, also appears to be acceptable.

However, this does not apply to non-stationary sensor arrangements such as are used for example in motor vehicles.

OBJECT OF THE INVENTION

Proceeding from the prior art described above, the invention is based on the problem of providing a sensor arrangement for determining the $CO_2$ concentration in an interior space that is able to be used without impairment of the measurement values that are able to be achieved also in non-stationary operation, for example in vehicles.

SUMMARY OF THE INVENTION

This problem is solved according to the invention in that the sensor arrangement has an evaluation unit that can calculate the air pressure from measurement values of the NDIR sensor unit and on the basis of the value calculated for the air pressure or respectively of an air pressure correction value calculated therefrom for the measurement value of the $CO_2$ concentration determined by the NDIR sensor unit, an air pressure compensation is able to be carried out. According to the invention, the knowledge is utilized that the $CO_2$ content in the atmosphere lies currently at approximately 400 ppm (mean value over a year), wherein seasonal fluctuations can occur that, however, are comparatively small. Owing to the small extent of these fluctuations, in the case of the sensor arrangement according to the invention a constant $CO_2$ concentration in the atmosphere is used as the basis with sufficient accuracy for the measurement purposes that are to be achieved. By means of the evaluation unit, taking as a basis a constant $CO_2$ content in the atmosphere, the number of $CO_2$ molecules is determined on the optical measuring section of the NDIR sensor unit. If, compared to a presettable value prevailing under normal conditions, deviations occur in the temperature-compensated value, depending on the direction of the deviation an increase or a lowering of the prevailing air pressure is inferred.

When the sensor arrangement according to the invention, in accordance with a further development, is provided with a temperature sensor that can determine the temperature in the interior space, and with a temperature compensation unit by means of which, on the basis of the measurement value determined by the temperature sensor, a temperature compensation is able to be carried out for the measurement value of the $CO_2$ concentration determined by the NDIR sensor unit, temperature fluctuations that can impair a correct determining of the $CO_2$ concentration in the air in the interior space can be compensated with a comparatively small effort.

For temperature compensation it is basically also conceivable to use an optical reference channel as reference value. Here, it is then assumed that the reference channel has the same temperature behavior as the measurement channel, whereby any temperature influences are eliminated in the calculation.

In order to achieve permanently reliable measurement results by the sensor arrangement according to the invention for determining the $CO_2$ concentration in an interior space, it is advantageous if, by means of the evaluation unit of the sensor arrangement, a ventilation system of the interior space is able to be adjusted so that the optical measuring section of the NDIR sensor unit is acted upon by exterior or respectively fresh air, and on the basis of the value calculated for the air pressure of the fresh air outside the interior space the air pressure correction value is able to be adapted for the air pressure compensation.

A particularly advantageous further development of the sensor arrangement according to the invention is achieved when a control apparatus is arranged downstream of the evaluation unit, by means of which control apparatus the ventilation system, associated with the interior space, is able to be switched over automatically to exterior or respectively fresh air supply to the optical measuring section of the NDIR sensor arrangement, as soon as the air-pressure-compensated measurement value of the $CO_2$ concentration calculated in the evaluation unit exceeds a presettable upper threshold value.

The evaluation unit of the sensor device according to the invention can advantageously be connected to the ventilation system of the interior space and from there can receive status information of the ventilation system, wherein this status information is taken into account in the calculation of the air pressure correction value.

As status information in particular data concerning the exchange of air between the interior space and the exterior air can be made available to the evaluation unit.

Expediently, a power level of a fan and/or the current proportion between circulating air and exterior air of the quantity of air introduced into the interior space and/or a degree of window opening and/or a degree of door opening and/or the vehicle speed can function as suitable parameters for corresponding status information that are passed on to the evaluation unit.

Furthermore, measurement values of an air quality sensor exposed to the exterior air can also be made available to the evaluation unit.

In order to guarantee a quick adaptation of the air pressure correction value to the actually prevailing conditions, it is advantageous if the NDIR sensor unit of the sensor arrangement is arranged in the interior space, preferably in an air outflow region of the ventilation system, so that it is able to be acted upon with the fresh air in the case of the feeding of fresh air into the interior space, before the fresh air mixes with the interior air present in the interior space.

In a further embodiment, the sensor arrangement according to the invention serves for the determining and compensation of the air pressure, wherein it has an NDIR (non-dispersive infrared spectroscopy) sensor unit, by means of which the number of $CO_2$ molecules is able to be determined on an optical measuring section, and an evaluation unit, by means of which the air pressure is able to be calculated from the measurement value of the NDIR sensor unit.

According to the invention, in a method for the compensation of air pressure changes in the determining of the $CO_2$ concentration in air, the $CO_2$ concentration is measured by means of an NDIR sensor unit, wherein in this method an evaluation unit is used, by means of which corresponding air pressure values are calculated from the measurement values of the NDIR sensor unit by mathematical methods.

BRIEF DESCRIPTION OF THE DRAWING

The invention is explained in further detail below with the air of an embodiment with reference to the drawings, the single FIGURE of which shows a schematic illustration of an embodiment of a sensor arrangement according to the invention for determining the $CO_2$ concentration in the air situated in an interior space.

SPECIFIC DESCRIPTION OF THE INVENTION

A sensor arrangement 1, illustrated in principle in the single FIGURE, for determining the $CO_2$ concentration in the air of an interior space has an NDIR (non-dispersive infrared spectroscopy) sensor unit 2, a temperature sensor 3, a temperature compensation unit 4 and an evaluation unit 5.

The sensor arrangement 1 is not stationary, i.e. it is arranged for example in a motor vehicle.

The NDIR sensor unit 2 does not react to the concentration of the $CO_2$, but rather to the number of $CO_2$ molecules in an optical measuring section of the NDIR sensor unit 2. A greater number of $CO_2$ molecules on the optical measuring section leads to a greater absorption of the amount of energy radiated by a radiation unit of the NDIR sensor unit 2 on the wavelength relevant for $CO_2$. Through this increased energy absorption, the actual measurement signal is weakened. From the level of the measurement signal, conclusions can be drawn accordingly concerning the $CO_2$ concentration in the air in which the optical measuring section of the NDIR sensor unit 2 is situated.

According to the general gas law, the number of molecules in an ideal gas depends on the temperature and the pressure. Accordingly, the temperature and the temperature have influences on the measurement value.

In order to compensate the influences of temperature changes, the sensor arrangement 1 has the temperature sensor 3 and the temperature compensation unit 4. By means of the temperature sensor 3, the temperature of the air in the interior space is determined and is passed on to the temperature compensation unit 4, in which the temperature influence on the measurement value indicating the $CO_2$ concentration is compensated. The measurement value MW1, adjusted accordingly with respect to temperature influences, is present at the outlet side of the temperature compensation unit 4.

In order to also eliminate the pressure influences on the measurement value ultimately indicating the $CO_2$ concentration, in the case of the sensor arrangement 1 shown in the single FIGURE provision is made to subject the measurement values of the NDIR sensor unit 2, which are characteristic for the number of $CO_2$ molecules on the optical measuring section of the NDIR sensor unit 2, to a processing in the evaluation unit 5. It is assumed here that the $CO_2$ content in the atmosphere lies today at approximately 400 ppm, this being a mean value here that is applicable for a year, which can fluctuate seasonally by approximately ±2 ppm. For the mathematical processing in the evaluation unit 5, one proceeds from a constant value for the $CO_2$ content in the atmosphere, and namely independently of the air pressure.

The NDIR sensor unit 2 is calibrated for the standard value SATP (Standard Ambient Temperature and Pressure) (298.15 K and 1 bar). The temperature compensation is carried out by means of the temperature sensor 2 and the temperature compensation unit 4 for each measurement value of the NDIR sensor unit 2. The measurement result available at the outlet side of the temperature compensation unit 4, in the form of the measurement values MW1, is therefore only still influenced by the air pressure.

The measurement value MW1 is stored in the evaluation unit 5 for a $CO_2$ concentration of 400 ppm.

All the measurement values MW1 that are smaller than the measurement value MW1 stored for the $CO_2$ concentration in the evaluation unit 5 are interpreted as a clear indication of an air pressure below the air pressure of 1 bar established for SAPT.

In the evaluation unit 5 in each operating period of the sensor arrangement 1 situated in a vehicle, the current measurement signal MW1 is compared with the stored smallest measurement signal MW1. When the current measurement signal MW1 is smaller than the stored measurement signal MW1, the current measurement signal MW1 is stored as the smallest measurement signal MW1.

The period of time between the switching on of the ignition and the switching off of the ignition can be selected for example as operating period in the vehicle. Often, the operating period of the sensor arrangement 1 runs beyond the moment of switching off the ignition, namely when the sensor arrangement 1 is also operated in the so-called ignition after-run.

The correction value for the pressure compensation is calculated from the respectively smallest measurement value MW1 during an operating period.

The evaluation unit 5 is integrated into the sensor arrangement 1. It can also be integrated into a signal chain arranged downstream. For this, an air-conditioning control unit of a motor vehicle presents itself, because usually the NDIR sensor unit 2 is connected electrically to this air-conditioning control unit. The pressure compensation can be technically integrated into the program sequence with comparatively little effort.

In this procedure, it is reliably prevented that a $CO_2$ alarm when traveling uphill or up a mountain pass is only triggered at $CO_2$ concentrations that are much too high. Through the air pressure that is almost halved for example at 5500 m above sea level, the NDIR sensor unit 2 would only trigger an alarm at twice as high $CO_2$ concentrations without the air pressure compensation in the evaluation unit 5. Also, the $CO_2$ concentration MW2 emitted from the sensor arrangement 1 would only be half as high as the actual $CO_2$ concentration.

In order to increase the reliability and the accuracy of the measurement of the actual $CO_2$ concentration, not only is simply a lowest measurement value MW1, determined on one occasion, used for the air pressure compensation, but several chronologically successive measurement values MW1 are determined and converted into a correction value according to a mathematical rule. For example, the averaging over a number of determined measurement values MW1 can function as the mathematical rule.

However, when traveling downhill or down a mountain pass, the evaluation unit 5 must also be able to react to the then increasing air pressure and adapt the correction signal accordingly, because otherwise the NDIR sensor unit 2 would permanently emit $CO_2$ concentrations that are too high and would trigger an alarm signal at distinctly lower $CO_2$ concentrations than provided.

The logic for an adaptation of the correction value in the direction of higher air pressures is far more complex than the adaptation in the other direction, because the measurement values MW1 can be increased for example by the breathing of occupants in the interior space of the motor vehicle over the background load of 400 ppm. For this reason, it is important to take into consideration the operating state of the ventilation system of the motor vehicle, in order to be able to make an assessment of the influence of the breathing of the breathing of the motor vehicle occupants on the $CO_2$ concentration.

Accordingly, the evaluation unit 5 contains status information for this of the ventilation system of the vehicle.

The most important status information is that concerning the air exchange between the interior space of the vehicle and the exterior air. For this, the power level of a fan of the ventilation system of the vehicle is reported to the evaluation unit 5. Furthermore, information is reported to the evaluation unit 5 as to the extent to which the ventilation system is in recirculating air operation or respectively to what percentage the recirculating air operation is activated or deactivated. Further status information passed on to the evaluation unit 5 concerns the degree of window opening and the degree of door opening. Furthermore, information obtained from an air quality sensor, exposed to the exterior air, concerning the quality of the exterior air can be passed on to the evaluation unit 5. Furthermore, speed data can also be passed on to the evaluation unit 5.

The NDIR sensor unit 2 should be arranged in the region of the air discharge installation of the ventilation system of the vehicle so that in fresh air operation it is acted upon as directly as possible by fresh air, before the fresh air mixes to an appreciable extent with air from the interior space of the vehicle.

When in the case of traveling downhill or down a mountain pass the air pressure increases and the $CO_2$ concentration apparently increases by means of the MW1, this leads over the course to a fresh air requirement through the NDIR sensor unit 2. When the evaluation unit 5 receives for example the following status information, namely as condition 1 the information that the vehicle is running, as condition 2 the information that the recirculating air operation is not activated, and as condition 3 the information that the fan of the ventilation system of the vehicle is running, it can conclude that the $CO_2$ concentration corresponds substantially to the $CO_2$ concentration of the exterior air, so that the correction value can be adapted according to this $CO_2$ concentration.

I claim:

1. A sensor arrangement for determining the $CO_2$ concentration in an interior space, the sensor arrangement comprising:
    an NDIR sensor unit capable of determining a number of $CO_2$ molecules on an optical measuring section and therefrom the $CO_2$ concentration in an interior space; and
    an evaluation unit for calculating air pressure from measurement values of the NDIR sensor unit and for conducting an air-pressure compensation on the basis of a value calculated for the air pressure or of an air pressure correction value calculated therefrom for measuring a $CO_2$ concentration determined by the NDIR sensor unit.

2. The sensor arrangement defined in claim 1, further comprising:
    a temperature sensor for determining a temperature in the interior space,
    a temperature compensation unit for, on the basis of the measurement value determined by the temperature sensor, conducting a temperature compensation for the measurement value of the $CO_2$ concentration determined by the NDIR sensor unit.

3. The sensor arrangement defined in claim 1, further comprising:
    a ventilation system for exposing the optical measuring section to fresh outside air such that, on the basis of the value calculated for the air pressure of the fresh air outside the interior space, the air pressure correction value is adapted for the air pressure compensation.

4. The sensor arrangement defined in claim 3, further comprising:
    a control apparatus downstream of the evaluation unit for automatically switching over the ventilation system associated with the interior space to feed fresh outside air to the optical measuring section of the NDIR sensor arrangement as soon as the air-pressure-compensated measurement value of the $CO_2$ concentration calculated in the evaluation unit exceeds a presettable upper threshold value.

5. The sensor arrangement defined in claim 3, wherein the NDIR sensor unit is in the interior space in an air outflow region of a ventilation system so that with the feeding of fresh air into the interior space it is acted upon by the fresh air before the fresh air mixes with the interior air in the interior space.

6. The sensor arrangement defined in claim 3, wherein the evaluation unit is connected to the ventilation system of the interior space, receives therefrom status information, and takes the received status information into consideration for calculating the air pressure correction value.

7. The sensor arrangement defined in claim 6, wherein data concerning air exchange between the interior space and the exterior are made available to the evaluation unit as the status information of the ventilation system.

8. The sensor arrangement defined in claim 6, wherein the status information is a power level of a fan or a current proportion between recirculating air and exterior air of the quantity of air introduced into the interior space or a degree of window opening or a degree of door opening or a vehicle speed.

9. The sensor arrangement defined in claim 6, wherein measurement values of an air quality sensor exposed to the exterior are made available to the evaluation unit.

10. A sensor arrangement for determining and compensating the air pressure, comprising:
   an NDIR sensor unit for determining a number of $CO_2$ molecules on an optical measuring section and
   an evaluation unit for calculating air pressure from number determined by the NDIR sensor unit.

11. A method of compensating for air pressure changes when determining a $CO_2$ concentration in air, the method comprising the steps of:
   measuring $CO_2$ concentration with an NDIR sensor unit; and
   mathematically converting the concentration determined by the NDIR sensor unit into an air pressure values in an evaluation unit.

\* \* \* \* \*